United States Patent [19]
Taylor, Jr. et al.

[11] Patent Number: 5,114,944
[45] Date of Patent: May 19, 1992

[54] 2-PHENYLPYRAZOLO[1,5-A]PYRIMIDINE-3-ACETIC ACID DERIVATIVES EXHIBITING THERAPEUTIC EFFECTS

[75] Inventors: Chandler R. Taylor, Jr., Mechanicsville; Harold F. Stauffer, Jr., Midlothian, both of Va.; Bruce E. Tomczuk, Fairport, N.Y.

[73] Assignee: A. H. Robins Company Incorporated, Richmond, Va.

[21] Appl. No.: 684,247

[22] Filed: Apr. 12, 1991

[51] Int. Cl.⁵ ............... C07D 487/04; A61K 31/505
[52] U.S. Cl. .................... 514/258; 544/281; 548/375; 548/377
[58] Field of Search .......... 544/281; 514/258

[56] References Cited

U.S. PATENT DOCUMENTS

| | | | |
|---|---|---|---|
| 4,048,184 | 9/1987 | Hoehn | 544/281 |
| 4,654,347 | 3/1987 | Dusza et al. | 544/281 |
| 5,057,534 | 10/1991 | Taylor et al. | 514/404 |

OTHER PUBLICATIONS

Med. Res. Rev. 1, 3 (1981).
J. Pharmacol. Exp. Ther. 96, 99 (1949).
Drug Dev. Res. 2, 383 (1982).
Psychopharmacology 21, 1 (1971).
Technometrics 6(3), 241 (1964).
J. Med. Chem. 10, 276 (1967).
J. Pharm. Sci. 53, 577 (1964).
Anxiolytics (Ed. S. Fielding) Futura Publ. Co. 41–81, 1979.
Psychopharmacology: A Review of Progress; U.S. Pub. Health Ser. No. 1836, 153–184 (1967).
The Benzodiazepines; Raven Press, N.Y. 461–488 (1973).
J. Pharmacol. Exp. Ther. 151, 369 (1966).

*Primary Examiner*—Mark L. Berch
*Assistant Examiner*—Jyothsna Venkat
*Attorney, Agent, or Firm*—A. S. Milowsky

[57] ABSTRACT

This invention provides a 2-arylpyrazolo[1,5-a]pyrimidine-3-acetic acid corresponding to the formula:

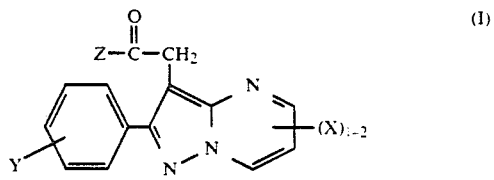

where X is hydrogen or a halogen, hydroxy, $C_1$–$C_4$ alkyl or $C_1$–$C_4$ alkoxy substituent; Y is hydrogen or a halogen, $C_1$–$C_4$ alkyl or $C_1$–$C_4$ alkoxy substituent; Z is a hydroxy, $C_1$–$C_4$ alkoxy or —NRR substituent; and R is hydrogen or a $C_1$–$C_4$ alkyl substituent; or a pharmaceutically acceptable salt thereof which is useful as a therapeutic agent which exhibits anxiolytic, anticonvulsant and muscle relaxant effects in a warm blooded animal.

23 Claims, No Drawings

2-PHENYLPYRAZOLO[1,5-A]PYRIMIDINE-3-ACETIC ACID DERIVATIVES EXHIBITING THERAPEUTIC EFFECTS

BACKGROUND OF THE INVENTION

The discovery of specific benzodiazepine binding sites on receptors in the brain has initiated a search for a possible "endogenous ligand" for the receptor sites.

Compounds found to bind to the benzodiazepine receptor sites include $N^6$-benzyladenosine, $\beta$-carbolines, zopiclone, nicotinamide, CL-218,872 (Lederle) and diazepam.

In the search for structural similarities between all of the benzodiazepine-receptor agonists and/or antagonists, a molecular overlap pattern has been developed and reported by P. Skolnick and S. Paul in Medicinal Research Reviews, 1, 3 (1981). The essential stereochemical parameters of the pattern are characteristic of compound structures such as imidazopyridines, azaindoles, pyrazolo[1,5-a]pyrimidines, and structure types corresponding to the compounds recited above.

There is continuing interest in the development of novel compounds which bind to the specific benzodiazepine binding sites, and which consequentially exhibit useful therapeutic activities.

Accordingly, it is an object of this invention to provide novel compounds which can function as endogeneous ligands for benzodiazepine binding sites in the brain.

It is another object of this invention to provide novel compounds which exhibit anxiolytic, anticonvulsant and muscle relaxant effects in warm blooded animals.

It is a further object of this invention to provide novel 2-arylpyrazolo[1,5-a]pyrimidine-3-acetic acid derivatives.

Other objects and advantages of the present invention shall become apparent from the accompanying description and examples.

DESCRIPTION OF THE INVENTION

One or more objects of the present invention are accomplished by the provision of 2-arylpyrazolo[1,5-a]pyrimidine-3-acetic acid derivatives corresponding to the formula:

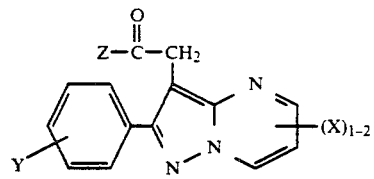

where X is hydrogen or a halogen, hydroxy, $C_1$-$C_4$ alkyl or $C_1$-$C_4$ alkoxy substituent; Y is hydrogen or a halogen, $C_1$-$C_4$ alkyl or $C_1$-$C_4$ alkoxy substituent; Z is a hydroxy, $C_1$-$C_4$ alkoxy or -NRR substituent; and R is hydrogen or a $C_1$-$C_4$ alkyl substituent; and pharmaceutically acceptable salts thereof.

Illustrative of halogen for X and Y in the above formula I are chlorine, bromine and fluorine. Suitable $C_1$-$C_4$ alkyl and $C_1$-$C_4$ alkoxy groups in Formula I include methyl, ethyl, propyl, isopropyl, butyl, isobutyl, methoxy, ethoxy, propoxy, butoxy, and the like.

The term "pharmaceutically acceptable acid addition salts" as employed herein refers to the acid addition salts, hydrates, alcoholates and salts of the compounds represented by Formula I which are physiologically compatible in warm blooded animals. The acid addition salts are formed with inorganic and organic acids such as hydrocholoric, sulfuric, phosphoric, fumaric, maleic, succinic, oxalic, citric, tartaric, cyclohexamic, and the like.

In another embodiment this invention provides a method for the treatment of warm blooded animals for anxiety symptoms which comprises internally administering to said animals a symptoms alleviating effective amount of a formulated 2-arylpyrazolo[1,5-a]pyrimidine-3-acetic acid derivative corresponding to Formula I as represented above.

In another embodiment this invention provides a method for the treatment of warm blooded animals for convulsion distress which comprises internally administering to said animals an anticonvulsant effective amount of a formulated 2-arylpyrazolo[1,5-a]pyrimidine-3-acetic acid derivative corresponding to Formula I as represented above.

In a further embodiment this invention provides a method for the treatment of warm blooded animals for muscular tension symptoms which comprises internally administering to said animals a symptoms alleviating effective amount of a formulated 2-arylpyrazolo[1,5-a]pyrimidine-3-acetic acid derivative corresponding to the Formula I as represented above.

A present invention formulated composition of a Formula I compound is administered to warm blooded animals in a wide variety of conventional pharmaceutical dosage forms, preferably in combination with a non-toxic pharmaceutical carrier. The active agent is administered orally, subcutaneously, intravenously or intramuscularly and, if necessary, in repeated doses until satisfactory response is obtained. The daily dosage is from about 5 to about 300 mg of active medication, advantageously from about 5 mg to 50 mg.

Compositions for oral administration can be in the form of elixers, capsules, tables or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in alleviation of symptoms associated with anxiety, muscular tension or convulsion disorders will be formulated to contain from about 0.1 mg/kg to about 3.0 mg/kg body weight, preferably 1.0 mg/kg body weight or less of a compound of Formula I.

In all of the above, it is only necessary that a suitable effective dosage is consistent with the dosage form employed. The exact individual dosages, as well as daily dosages, will be determined according to standard medical principles under the direction of a physician or veterinarian.

PREPARATION OF INVENTION COMPOUNDS

A 2-arylpyrazolo[1,5-a]pyrimidine-3-acetic acid derivative can be prepared from a substituted aroyl propionate by the following sequence of synthesis procedures:

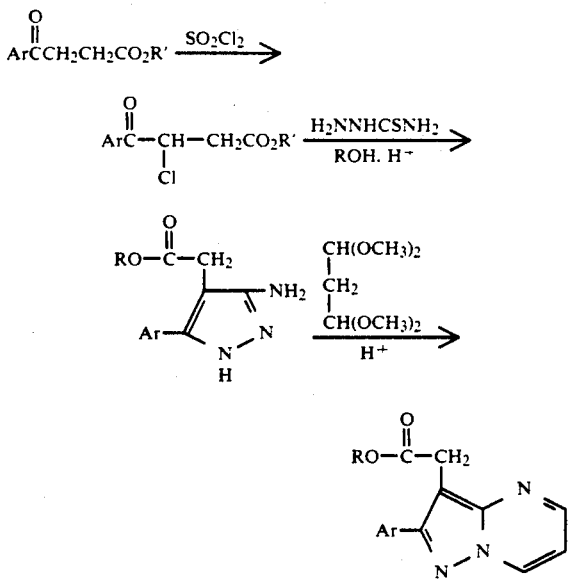

The following examples are further illustrative of the present invention. The components and specific ingredients are presented as being typical, and various modification can be derived in view of the foregoing disclosure within the scope of the invention.

INTERMEDIATE PREPARATIONS

Preparation 1

3-Amino-5-phenyl-1H-pyrazole-4-acetic acid butyl ester ethanedioate

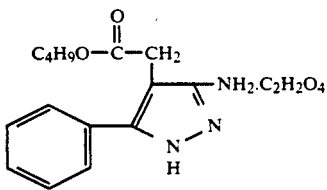

A mixture of 10.0 g (0.044 mole) of methyl-3-benzoyl-3-chloropropionate and 4.0 g (0.044 mole) of thiosemicarbazide in 50 ml of 1-butanol was refluxed under a nitrogen atmosphere for 32 hours. After cooling to room temperature, the precipitated sulfur was removed by filtration. The filtrate was evaporated under reduced pressure and the residue partitioned between methylene chloride and aqueous 7% sodium bicarbonate. The layers were separated and the organic layer was extracted with water, dried over magnesium sulfate and evaporated under reduced pressure. The residue was dissolved in toluene and chromatographed on an 85 g column of silica gel (47 mm × 20 cm) packed in toluene. The column was washed with toluene, methylene chloride, 10% and 50% ethyl acetate-methylene chloride and ethyl acetate, respectively. The fractions containing relatively pure products were combined and evaporated under reduced pressure. The residual oil (4.7 g) was dissolved in isopropanol and treated with 1.5 g (0.017 mole) of anhydrous oxalic acid. The mixture was refluxed until solution was complete, filtered, and the filtrate was treated with isopropyl ether to the cloud point. The oxalate salt of the butyl ester was collected by filtration: 4.8 g (30%), mp 169°-172° C.

Analysis Calc. for $C_{15}H_{19}N_3O_2 \cdot C_2H_2O_4$: C, 56.19; H, 5.83; N, 11.56. Found: C, 56.18; H, 5.84; N, 11.54.

Preparation 2

3-Amino-5-(4-methoxyphenyl)-1H-pyrazol-4-acetic acid butyl ester ethanedioate (1:1)

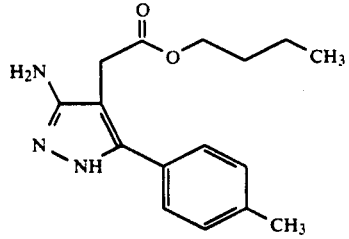

A stirred slurry of 45.6 g (0.5 mol) of thiosemicarbazide in 1200 mL of 1-butanol was treated with 41 mL (0.5 mol) of hydrochloric acid (37%), then stirred for 30 minutes. The reaction mixture was treated with 120.4 g (0.5 mol) of 3-chloro-3-(4-methylbenzoyl)propionic acid methyl ester added in a steady stream and stirred at ambient temperature for 4 hours, then heated at reflux for 16 hours to give a clear orange-brown solution. The reaction mixture was heated for 4 hours while water was azetroped from the reaction. Upon cooling the reaction mixture, sulfur precipitated and was removed by filtration. The filtrate was concentrated in vacuo to an amber residue (185.4 g). The residue was dissolved in 2-propyl ether, and 45 g of oxalic acid in acetone was added and stirred for 18 hours. Filtration yielded 155 g of wet crude product as the oxalate salt. The crude product was dried to a tan powder to yield 112 g (59.4%). A sample was recrystallized from methyl isobutyl ketone for elemental analysis, mp 150°-151° C.

Analysis Calc. for $C_{16}H_{21}N_3O_2 \cdot C_2H_2O_4$: C, 57.29; H, 6.14; N, 11.13. Found: C, 57.11; H, 6.08; N, 11.01.

Preparation 3

2-(4-Methylphenyl)pyrazolo[1.5-a]pyrimidine-3-acetic acid ethyl ester

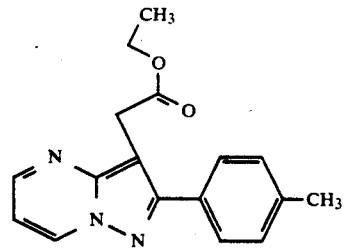

A stirred slurry of 50.2 g (0.133 mole) of 3-amino-5-(4-methylphenyl)-1H-pyrazole-4-acetic acid butyl ester ethanedioate (1:1) in 500 mL of 190 ethanol was treated first with 5 mL of hydrochloric acid (37%) and then with 21.8 g (0.133 mole) of malonaldehyde bis(dimethyl acetal). After stirring for 24 hours at ambient temperature, the reaction mixture was concentrated in vacuo. The residue was dissolved in 500 mL of methylene chloride and washed with saturated sodium bicarbonate solution. The combined aqueous layers were extracted with methylene chloride then the methylene chloride solutions were combined and washed with water. After drying the methylene chloride solution was concentrated in vacuo. The residue was dissolved in 500 mL of 200 ethanol, treated with 1 mL of concentrated sulfuric acid, and heated on a steam bath for 24 hours. The ethanol solution was treated with 50 g of potassium carbonate and 5 mL of $H_2O$. After stirring for 30 minutes, the inorganic material was removed by filtration and the filtrate concentrated in vacuo to a black tar-like residue. The residue was dissolved in 2-propyl ether, filtered, and treated with ethereal hydrogen chloride. The salt which precipitated was collected by filtration, yielding 44 g of crude yellow-green product. The crude product was dissolved in 190 ethanol, diluted with water, then treated with 20 g of potassium carbonate. The precipitated product was collected by filtration in 2 batches to yield 33.4 g (85%) of tan product, mp 69°–71.5° C. An analytical sample was recrystallized from ethanol-water with charcoal treatment yielding a pale yellow crystalline powder, mp 71°–73° C.

Analysis Calc. for $C_{17}H_{17}N_3O_2$: C, 69.14; H, 5.80; N, 14.23. Found: C, 68.94; H, 5.73; N, 14.02.

Preparation 4

2-(4-Methylphenyl)pyrazolo[1,5-a]pyrimidine-3-acetic acid

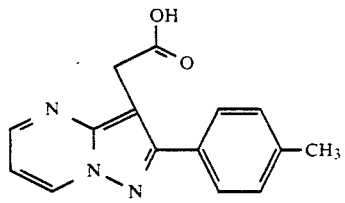

A stirred mixture of 32.5 g (0.11 mole) of 2-(4-methylphenyl)pyrazolo[1,5-a]pyrimidine-3-acetic acid ethyl ester and 4.5 g (0.11 mole) of sodium hydroxide in 150 mL of 190 ethanol was heated until the material dissolved. After cooling, the reaction mixture was diluted with an equal volume of water, heated until a clear dark brown solution was obtained, then cooled by stirring overnight. The reaction mixture was diluted with an additional 300 mL of water and acidified to pH 6 with glacial acetic acid. The milky solution yielded 27 g (90%) of brown crystalline product, mp 170°–171°. An analytical sample recrystallized from acetonitrile-water yielding pale yellow crystals, mp. 172°–173° C.

Analysis Calc. for $C_{15}H_{13}N_3O_2$: C, 67.41; H, 4.90; N, 15.72. Found: C, 67.31; H, 4.82; N, 15.75.

EXAMPLE I

2-Phenylpyrazolo[1,5-a]pyrimidine-3-acetic acid ethyl ester

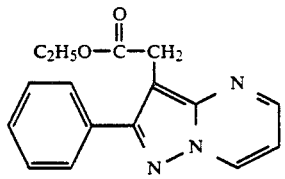

A mixture of 4.7 g (0.013 mole) of 3-amino-5-phenyl-1H-pyrazole-4-acetic acid butyl ester and 2.15 g (0.013 mole) of malonaldehyde bis(dimethylacetal) in 100 ml of absolute ethanol was treated with 3 ml of concentrated hydrochloric acid and 3 ml of water and stirred for about 20 hours. The solvent was evaporated under reduced pressure and the residue partitioned between methylene chloride (100 ml) and aqueous 7% sodium bicarbonate (100 ml). The layers were separated and the organic layer was extracted with water (100 ml), dried over magnesium sulfate and evaporated under reduced pressure.

The residue (4.3 g) was dissolved in 100 ml of absolute ethanol, acidified with 3 drops of concentrated sulfuric acid, stirred for 16 hours at room temperature, and then heated at reflux for 16 hours. The solvent was evaporated under reduced pressure and the residue dissolved in methylene chloride, extracted with aqueous 7% sodium bicarbonate, dried over magnesium sulfate and evaporated under reduced pressure (3.8 g). The residual oil was crystallized in and recrystallized from isopropyl ether to give 1.84 g of product, mp 86°–89° C.(50%).

Analysis Calc. for $C_{16}H_{15}N_3O_2$: C, 68.31; H, 5.37; N, 14.93. Found: C, 68.16; H, 5.35; N, 14.87.

EXAMPLE II

2-Phenylpyrazolo[1,5-a]pyrimidine-3-acetic acid

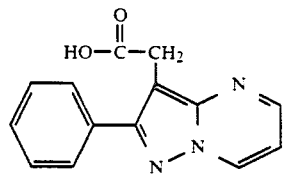

A solution of 12.25 g (0.043 mole) of 2-phenylpyrazolo[1,5-a]pyrimidine-3-acetic acid ethyl ester in 100 ml of absolute ethanol was treated with 6.9 g (0.087 mole) of 50% sodium hydroxide and 35 ml of water and refluxed for 4 hours under a nitrogen atmosphere. The solvent was evaporated under reduced pressure and the residue was dissolved in water (100 ml). Acidification with glacial acetic acid produced a solid precipitate. The solid was collected by filtration to yield 10.8 g of crude product, mp 78°–90° C. Recrystallization from acetone-water, and then from toluene provided 8.25 g (75%) of product, mp 153°–156° C.

Analysis Calc. for $C_{14}H_{11}N_3O_2$: C, 66.39; H, 4.37; N, 16.59. Found: C, 66.10; H, 4.33; N, 16.45.

EXAMPLE III

N,N-Dimethyl-2-phenylpyrazolo[1,5-a]pyrimidine-3-acetamide

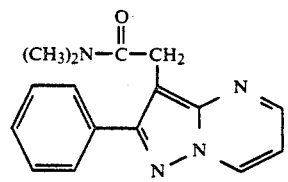

A mixture of 3.5 g (0.013 mole) of 2-phenylpyrazolo[1,5-a]pyrimidine-3-acetic acid and 2.24 g (0.013 mole) of 1,1'-carbonyldiimidazole in 150 ml of anhydrous tetrahydrofuran was stirred for 4 hours under a nitrogen atmosphere. A solution of dimethylamine in tetrahydrofuran (14.0 ml of a 2.95M solution; 0.0414 mole) was added. The mixture was stirred at room temperature for one hour. The solvent was evaporated under reduced pressure, and the residue was dissolved in methylene chloride (100 ml). The solution was extracted with 7% aqueous sodium bicarbonate, and with water, and then dried over anhydrous magnesium sulfate and evaporated under reduced pressure. The crystalline residue (4.6 g) was recrystallized from isopropanol to give 2.77 g (72%) of product, mp 156°-157.5° C.

Analysis Calc. for $C_{16}H_{16}N_4O$: C, 68.55; H, 5.75; N, 19.98. Found: C, 68.49; H, 5.74; N, 19.92.

EXAMPLE IV

N-Methyl-2-phenylpyrazolo[1,5-a]pyrimidine-3-acetamide

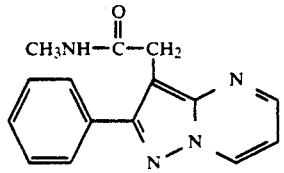

A mixture of 3.5 g (0.013 mole) of 2-phenylpyrazolo[1,5-a]pyrimidine-3-acetic acid and 2.24 g (0.013 mole) of 1,1'-carbonyldiimidazole in 150 ml of anhydrous tetrahydrofuran was stirred for 3 hours under a nitrogen atmosphere. A solution of monoethylamine in tetrahydrofuran (16 ml; 0.041 mole; 2.59M) was added, and the mixture was stirred at room temperature for one hour. Water (50 ml) was added to dissolve a precipitate that had formed. The solvents were evaporated under reduced pressure, and the residue was triturated in isopropanol to give 2.96 g of solid, mp 211°-213° C. Recrystallization from a mixture of isopropanol and water provided 2.58 g (70%) of product, mp 212°-214° C.

Analysis Calc. for $C_{15}H_{14}N_4O$: C, 67.65; H, 5.29; N, 21.03. Found: C, 67.50; H, 5.26; N, 20.92.

EXAMPLE V

2-Phenylpyrazolo[1,5-a]pyrimidine-3-acetamide

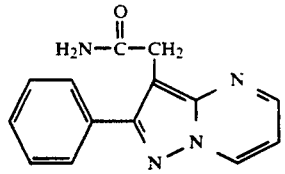

A mixture of 3.5 g (0.013 mole) of 2-phenylpyrazolo[1,5-a]pyrimidine-3-acetic acid and 2.24 g (0.013 mole) of 1,1'-carbonyldiimidazole in 150 ml of anhydrous tetrahydrofuran was stirred for 3 hours at room temperature while nitrogen was bubbled through the mixture. The reaction mixture was cooled in a dry ice/acetone bath, and treated with 50 ml of liquid ammonia. The reaction mixture was warmed to room temperature and stirred for two days. The suspended solid which formed was collected by filtration (2.81 g, mp 204°-219° C.) combined with the residue from evaporation of the filtrate (3.1 g), and recrystallized from ethanol to give 2.1 g of product (60%), mp 217°-219° C.

Analysis Calc. for $C_{14}H_{12}N_4O$: C, 66.65; H, 4.79; N, 22.20. Found: C, 66.35; H, 4.72; N, 21.97.

EXAMPLE VI

2-Phenyl-N,N-dipropylpyrazolo[1,5-a]pyrimidine-3-acetamide

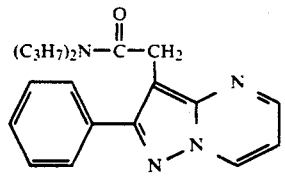

A mixture of 3.5 g (0.013 mole) of 2-phenylpyrazolo[1,5-a]pyrimidine-3-acetic acid and 2.24 g (0.013 mole) of 1,1'-carbonyldiimidazole in 150 ml of anhydrous tetrahydrofuran was stirred for 4 hours at room temperature while nitrogen was bubbled through the mixture. After additional stirring, a solution of 4.19 g (0.041 mole) of di-n-propylamine in 10 ml of anhydrous tetrahydrofuran was added dropwise and the mixture was stirred for about 17 hours under a nitrogen atmosphere. The solvent was evaporated under reduced pressure and the residue (7.3 g) was recrystallized from ethanol-water to give 3.3 g of product (72%), mp 103°-105° C.

Analysis Calc. for $C_{20}H_{24}N_4O$: C, 71.40; H, 7.19; N, 16.65. Found: C, 71.21; H, 7.18; N, 16.55.

EXAMPLE VII 2-(4-Chlorophenyl)pyrazolo[1,5-a]pyrimidine-3-acetic acid ethyl ester

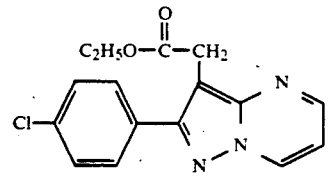

A suspension of 23.0 g (0.057 mole) of 3-amino-5-(4-chlorophenyl)-1H-pyrazole-4-acetic acid butyl ester ethanedioate and 9.6 g (0.057 mole) of malonaldehyde bis(dimethylacetal) (99%) in 250 ml of absolute ethanol was treated with 5 ml of concentrated hydrochloric acid and 10 ml of water.

Following the procedure of Example I, the ester product (20.6 g) was recovered and recrystallized from isopropyl ether to yield 14.6 g (80%), mp 94°-95.5° C.

Analysis Calc. for $C_{16}H_{14}ClN_3O_2$: C, 60.86; H, 4.46; N, 13.30. Found: C, 60.85; H, 4.42; N, 13.28.

EXAMPLE VIII 5,7-Dimethyl-2-phenylpyrazolo[1,5-a]pyrimidine-3-acetic acid ethyl ester

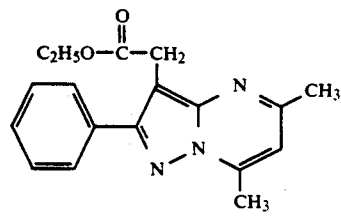

A mixture of 20.0 g (0.055 mole) of 3-amino-5-phenyl-1H-pyrazole-4-acetic acid butyl ester ethanedioate and 5.51 g (0.055 mole) of pentane-2,4-dione in 150 ml of 200 ethanol was treated with 10 ml of concentrated hydrochloric acid and stirred at room temperature for 17 hours.

Following the procedure of Example I, the ester product (18.8 g) was recovered and recrystallized from isopropyl ether to yield 12.6 g (74%), mp 104°–106° C.

Analysis Calc. for $C_{18}H_{19}N_3O_2$: C, 69.88; H, 6.19; N, 13.58. Found: C, 69.92; H, 6.26; N, 13.57.

EXAMPLE IX 2-(4-Chlorophenyl)pyrazolo[1,5-a]pyrimidine-3-acetic acid ethyl ester

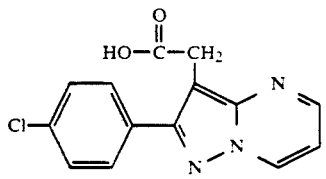

A suspension of 12.6 g (0.04 mole) of 2-(4-chlorophenyl)pyrazolo[1,5-a]pyrimidine-3-acetic acid ethyl ester in 100 ml of absolute ethanol was treated with 6.4 g (0.08 mole) of 50% sodium hydroxide and 35 ml of water. After refluxing for 5 hours, the mixture was stirred at room temperature for 48 hours. The precipitated solids were collected but due to hygroscopicity were dissolved in water, combined with the alcoholic filtrate and the solvents evaporated under reduced pressure. The residue was dissolved in warm water, acidified with glacial acetic acid and the medium crystallized on standing. The solid was collected by filtration, and recrystallized from isopropanol to give 9.4 g (82%) of product, mp 221°–225° C.

Analysis Calc. for $C_{14}H_{10}N_3O_2$: C, 58.44; H, 3.50; N, 14.60. Found: C, 58.37; H, 3.47; N, 14.55.

EXAMPLE X 2-(4-Chlorophenyl)N-methylpyrazolo[1,5a]pyrimidine-3-acetamide

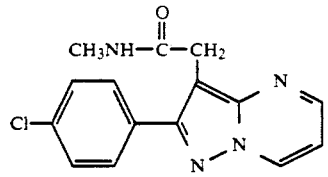

A mixture of 4.0 g (0.013 mole) of 2-(4-chlorophenyl)pyrazolo[1,5-a-]pyrimidine-3-acetic acid and 2.25 g (0.013 mole) of 1,1′carbonyldiimidazole in 150 ml of anhydrous tetrahydrofuran was stirred for 4 hours while a stream of nitrogen was bubbled through the mixture. A solution of monomethylamine in tetrahydrofuran (16.1 ml; 0.042 mole; 2.59M) was added, and the mixture was stirred at room temperature for 17 hours. A solid which formed was collected by filtration (3.39 g, mp 196°–202° C.), and recrystallized from isopropanol to give 3.6 g (88%) of product, mp 208°–210° C.

Analysis Calc. for $C_{15}H_{13}ClN_4O$: C, 59.90; H, 4.35; N, 18.62. Found: C, 59.84; H, 4.34; N, 18.50.

EXAMPLE XI 2-(4-Chlorophenyl)-N,N-dimethylpyrazolo[1,5-a]pyrimidine-3-acetamide

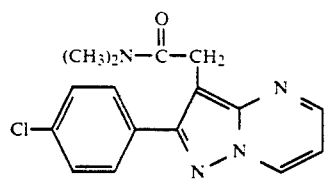

A mixture of 4.0 g (0.013 mole) of 2-(4-chlorophenyl)pyrazolo[1,5-a]pyrimidine-3-acetic acid and 2.25 g (0.013 mole) of 1,1′carbonyldiimidazole in 150 ml of anhydrous tetrahydrofuran was stirred for 4 hours while a stream of nitrogen was bubbled through the mixture. A solution of dimethylamine in tetrahydrofuran (14.1 ml; 0.0417 mole; 2.59M) was added, and the reaction was stirred for 17 hours under nitrogen atmosphere. The solvent was evaporated under reduced pressure and the residue was dissolved in dichloromethane, washed with water, aqueous 7% sodium bicarbonate, and water, and dried over magnesium sulfate and re-evaporated under reduced pressure. The crystalline residue (4.0 g) was recrystallized from isopropanol to give 3.4 g (79%) of product, mp 174°–175.5° C.

Analysis Calc. for $C_{16}H_{15}ClN_4O$: C, 61.05; H, 4.80; N, 17.79. Found: C, 60.95; H, 4.82; N, 17.75.

EXAMPLE XII 2-(4-Chlorophenyl)-5,7-dimethylpyrazolo[1,5-a]pyrimidine-3-acetic acid ethyl ester

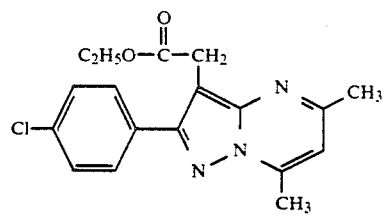

A solution of 35.5 g (0.089 mole) of 3-amino-5-(4-chlorophenyl)-1H-pyrazole-4-acetic acid butyl ester ethanedioate, 8.9 g (0.089 mole) of pentane-2,4-dione, and 10 ml of concentrated hydrochloric acid was stirred at room temperature for 17 hours under a nitrogen atmosphere.

Following the procedure of Example 1, the ester product (26.2 g) was recovered, mp 95°–102° C. A sample was recrystallized from absolute ethanol to give a purified product, 101.5°–102.5° C.

Analysis Calc. for $C_{18}H_{18}N_3O_2$: C, 62.88; H, 5.27; N, 12.22. Found: C, 62.55; H, 5.40; N, 11.14.

EXAMPLE XIII

N,N,5,7-Tetramethyl-2-phenylpyrazolo[1,5-a]pyrimidine-3-acetamide

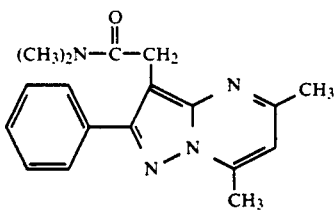

A suspension of 3.0 g (0.011 mole) of 5,7-dimethyl-2-phenylpyrazolo[1,5-a]pyrimidine-3-acetic acid and 1.73 g (0.011 mole) of 1,1'-carbonyldiimidazole in 120 ml of anhydrous tetrahydrofuran was stirred for 4 hours at room temperature while a stream of nitrogen was bubbled through the mixture. The solution was treated with a solution of dimethylamine in tetrahydrofuran (11.2 ml; 0.033 mole; 2.95M) and the mixture was stirred at room temperature for 17 hours under nitrogen. The solvent was evaporated under reduced pressure, and the residue was dissolved in dichloromethane, extracted with aqueous 7% sodium bicarbonate, and with water, dried over magnesium sulfate and evaporated under reduced pressure (4.5 g). The residue was recrystallized from isopropanol to give 2.1 g (62%) of product, mp 171°–172° C.

Analysis Calc. for $C_{18}H_{20}N_4O$: C, 70.10; H, 6.53; N, 18.16. Found: C, 70.08; H, 6.55; N, 18.14.

EXAMPLE XIV

N,5,7-Trimethyl-2-phenylpyrazolo[1,5-a]pyrimidine-3-acetamide

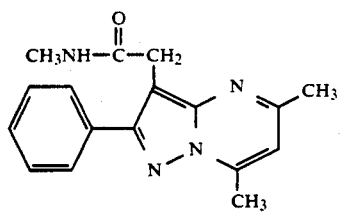

A suspension of 3.0 g (0.011 mole) of 5,7-dimethyl-2-phenylpyrazolo[1,5-a]pyrimidine-3-acetic acid and 1.73 g (0.011 mole) of 1,1'-carbonyldiimidazole in 120 ml of anhydrous tetrahydrofuran was stirred at room temperature for 4 hours while a stream of nitrogen was bubbled through the mixture. The clear solution which formed was treated with a solution of monomethylamine in tetrahydrofuran (12.8 ml; 0.033 mole; 2.59M) and the mixture stirred at room temperature for 17 hours under nitrogen.

Following the procedure of Example IV, a crude product was recovered and recrystallized from isopropanol to give 2.0 g (62.5%) of product, mp 180°–181° C.

Analysis Calc. for $C_{17}H_{18}N_4O$: C, 69.36; H, 6.16; N, 19.03. Found: C, 69.26; H, 6.16; N, 19.05.

EXAMPLE XV

6-Chloro-2-(4-chlorophenyl)pyrazolo[1.5-a]pyrimidine-3-acetic acid ethyl ester

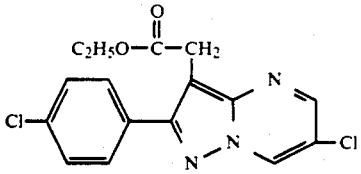

A solution of 3.2 g (0.01 mole) of 2(4-chlorophenyl)pyrazolo[1,5-a]pyrimidine-3-acetic acid ethyl ester in 30 ml of methylene chloride was stirred under nitrogen and cooled to 0° C. in an ice bath. The cooled reaction solution was treated with 1.4 g (0.84 ml) (0.01 mole) of sulfuryl chloride and the reaction was allowed to warm to room temperature. The reaction mixture was concentrated in vacuo and the residue dissolved in 20 ml of methylene chloride, and washed successively with water, saturated sodium carbonate solution, and water, and then concentrated in vacuo to obtain 3.5 of residue. The crude residue was placed on on a 100 g silica gel column and chromatographed with a methanol:benzene gradient (0–4%). Concentration of combined fractions yielded a solid which was recrystallized from benzene (300 mg). A second crop obtained after adding ligroin amounted to 1.1 g of mixed product. The combined residues recrystallized from ethanol to yield 1.3 g (37%) of long pale yellow needles, mp 139°–140° C.

Analysis Calc. for $C_{16}H_{13}Cl_2N_3O_2$: C, 54.88; H, 3.74; N, 12.00. Found: C, 54.73; H, 3.62; N, 11.97.

EXAMPLE XVI 2-(4-Chlorophenyl)pyrazolo[1.5-a]pyrimidine-3-acetamide

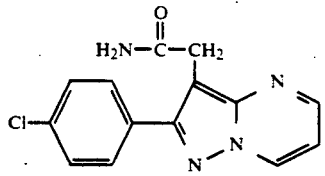

A stirred slurry of 3.5 g (0.012 mole) of 2-(4-chlorophenyl)pyrazolo[1,5-a]pyrimidine-3-acetic acid in 150 ml of dry tetrahydrofuran was treated with 3.2 g (0.015M) of 75% 1,1'-carbonyldiimidazole. After stirring for 30 minutes, nitrogen was bubbled through the reaction mixture for 3 hours, then 3 ml of anhydrous ammonia in 10 ml of tetrahydrofuran was added and stirring was continued for 16 hours.

Following the procedure of Example V, a crude product (3.6 g) was recovered and recrystallized from ethanol, yielding two crystalline forms. Proton nmr and mass spectra indicated that the two crystalline forms were the title product. Recrystallization of one of the two solids from ethanol yielded 1.5 g of fine white crystals, mp 220°–221° C.

Analysis Calc. for $C_{14}H_{11}ClN_4O$: C, 58.65; H, 3.87; N, 19.54. Found: C, 58.46; H, 3.72; N, 19.40.

EXAMPLE XVII 2-(4-Chlorophenyl-N,N-dipropylpyrazolo[1,5-a]pyrimidine-3-acetamide

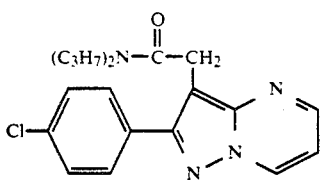

A mixture of 3.5 g (0.012 mole) of 2-(4-chlorophenyl)pyrazolo[1,5-a]pyrimidine-3-acetic acid and 3.2 g (0.015M) of 1,1'-carbonyldiimidazole (75%) in 150 ml of dry tetrahydrofuran was stirred under nitrogen for 30 minutes, then nitrogen was bubbled through the solution for 3 hours. The reaction mixture was treated with 1.2 g (0.012 mole) of dipropylamine and stirred for 16 hours. The reaction mixture was concentrated in vacuo. The crude residue was dissolved in 50 ml of methylene chloride and washed with water, saturated sodium bicarbonate, and again with water, then dried over magnesium sulfate and concentrated in vacuo to a solid residue (3.9 g). Recrystallization from 2-propyl ether:-hexane yielded 3.4 g (76.4%) of pale yellow crystals, mp 104°–106° C.

Analysis Calc. for $C_{20}H_{23}ClN_4O$: C, 64.77; H, 6.25; N, 15.11. Found: C, 64.64; H, 6.21; N, 15.05.

EXAMPLE XVIII 2-(4-Methylphenyl)-N,N-dipropylpyrazolo[1,5-a]pyrimidine-3-acetamide

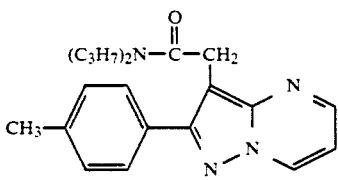

A mixture of 3.25 g (0.010 mole) of 3-[2-(1H-imidazole-1-yl)-2-oxoethyl]-2-(4-methylphenyl)-pyrazolo[1,5-a]pyrimidine (prepared from 2-(4-methylphenyl)pyrazolo[1,5-a]pyrimidine-3-acetic acid and 1,1'-carbonyldiimidazole) and 1.1 g (0.011 mole) of dipropylamine in 25 ml of benzene was stirred at reflux for 5 hours. After cooling, the reaction mixture was washed with water, dried over magnesium sulfate, and concentrated in vacuo (2.6 g). The crude solid residue was purified by a liquid-solid extraction with isopropyl ether in a soxhlet. The purified product was collected by filtration from the isopropyl ether (extraction solvent) to yield 1.4 g (39.6%) of golden yellow crystals, mp 110°–111° C.

Analysis Calc. for $C_{21}H_{26}N_4O$: C, 71.97; H, 7.48; N, 15.99. Found: C, 71.86; H, 7.52; N, 15.98.

EXAMPLE XIX

N-Methyl-2-(4-methylphenyl)pyrazolo[1,5-a]pyrimidine-3-acetamide

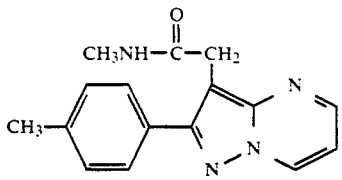

A stirred slurry of 3.2 g (0.010 mole) of 3-[2-(1H-imidazole-1-yl)-2-oxoethyl]-2-(4-methylphenyl)-pyrazolo[1,5-a]pyrimidine (prepared from 2-(4-methylphenyl)pyrazolo[1,5-a]pyrimidine-3-acetic acid and 1,1'-carbonyldiimidazole) in 20 ml of dry tetrahydrofuran was treated with 3 ml of monomethylamine in 10 ml of dry tetrahydrofuran added dropwise from a needle and syringe. After stirring for 36 hours the reaction mixture was diluted with 100 ml of water and the resulting solid collected by filtration (1.7 g). The crude product was recrystallized from acetonitrile to yield 1.1 g (38.9%) of beige crystals, mp 207°–208° C.

Analysis Calc. for $C_{16}H_{16}N_4O$: C, 68.55; H, 5.75; N, 19.99. Found: C, 68.67; H, 5.72; N, 20.12.

EXAMPLE XX 2-(4-Methylphenyl)pyrazolo[1,5-a]pyrimidine-3-acetamide

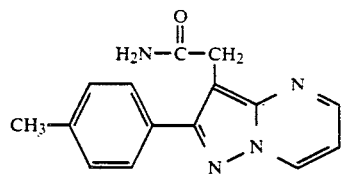

A stirred slurry of 3.2 g (0.010 mole) of 3-[2-(1H-imidazole-1-yl)-2-oxoethyl]-2-(4-methylphenyl)-pyrazolo[1,5-a]pyrimidine (prepared from 2-(4-methylphenyl)pyrazolo[1,5-a]pyrimidine-3-acetic acid and 1,1'-carbonyldiimidazol) in 20 ml of dry tetrahydrofuran was treated with 3 ml of ammonia in 10 ml of dry tetrahydrofuran. After stirring for 16 hours, the reaction mixture was diluted with 100 ml of water and the precipitated solid collected by filtration (1.6 g). The crude product was recrystallized from acetonitrile to yield 1.1 g (40.9%) of pale yellow crystals, mp 225°–226° C.

Anal. Calc. for $C_{15}H_{14}N_4O$: C, 67.66; H, 5.30; N, 21.04. Found: C, 67.05; H, 5.24; N, 21.09.

EXAMPLE XXI

N,N-Dimethyl-2-(4-methylphenyl)pyrazolo[1,5-a]pyrimidine-3-acetamide

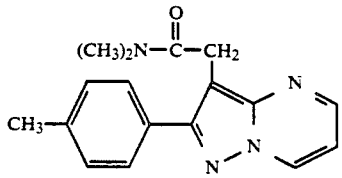

A stirred slurry of 3.2 g (0.010 mole) of 3-[2-(1H-imidazole-1-yl)-2-oxoethyl]-2-(4-methylphenyl)-pyrazolo[1,5-a]pyrimidine (prepared from 2-(4-methylphenyl)pyrazolo[1,5-a]pyrimidine-3-acetic acid and 1,1'-carbonyldiimidazole) in 20 ml of dry tetrahydrofuran was treated with 3 ml of dimethylamine in 10 ml of dry tetrahydrofuran. After stirring for 16 hours, the reaction mixture was diluted with 100 ml of water and the precipitated solid collected by filtration (1.4 g). The crude product was purified by a liquid-solid extraction in a soxhlet using isopropyl ether as the extracting solvent. Filtration yielded 1.6 g (33.6%) of golden yellow crystals, mp 163.5°–165° C.

Analysis Calc. for $C_{17}H_{18}N_4O$: C, 69.37; H, 6.16; N, 19.03. Found: C, 69.19; H, 6.12; N, 18.94.

PHARMACOLOGY

A. Anticonvulsant Activity Test

1. Metrazol ® Chemical Challenge Swinyard Method

Groups of 8 adult female mice were randomly assigned to dosage groups according to the method of Steel, R. G. D., and Torrie, J. H. in "Principles and Procedures of Statistics", McGraw-Hill Book Company, Inc., pp 99–100, pp 428–31 (1960). Each mouse was identified with a color code on its tail. The test compounds were administered as solutions or suspensions in 10 ml/kg mouse body weight of 0.5% aqueous methyl cellulose within 15 minutes of preparation of the suspension. Metrazol ® (pentylenetetrazol) was prepared as a solution in physiological saline. The mice were not fasted prior to the test. Eight mice were tested at each dosage level.

Each mouse received one dose of the test drug (usually 100 mg/kg for screening) in the 0.5% aqueous methylcellulose or the control article (0.5% aqueous methylcellulose alone) intraperitoneally. Metrazol ® (80 mg/kg S.C.) was then given in a loose fold of skin on the back of the neck 0.5 hour after the test compound or control article was administered. Injections were given with a 1 ml glass tuberculin syringe with an appropriate size hypodermic needle (27 gauge for solutions; 23 gauge for suspensions). All injections were given in a volume of 10 ml/kg mouse body weight. Each mouse was observed for 30 minutes following Metrazol ® injection. Failure of the animals to exhibit a threshold seizure (a single episode of clonic spasms at least 5 seconds in duration) was defined as protection. Anticonvulsant data were tabulated as the percent protection:

$$\frac{\text{No. Mice Protected}}{\text{No. Mice Tested}} \times 100.$$

The $ED_{50}$, 95% confidence limits and potency ratio may be ascertained by the computer-based probit analysis ascribed to Finney, D. J. in *Statistical Method in Biological Assay*, 2nd Ed., New York, 1964 (Hefner Publishing Co.).

2. Electrical Challenge

Adult female mice in groups of eight were administered the test drug intraperitoneally (usually 100 mg/kg initially for screening) in liquid carrier, usually 0.5% aqueous methyl cellulose or physiological saline. Animals were challenged electrically 0.5 hour after administration of test substance by placing brass electrodes on the corneas and applying an electrical stimulus (60 Hz, 8 msec. pulse width, 34 mA intensity) for 0.2 seconds by way of a Grass Stimulator ® and constant current unit and a Hunter Timer ®. The absence of tonic seizures upon cessation of the stimuli was scored as protection in that animal. The number of animals protected from tonic seizures at a given dose of test drug was determined. The $ED_{50}$, 95% confidence limits and potency ratio may be ascertained by the method of J. T. Litchfield and F. Wilcoxon J. PHARMACOL. EXP. THER. 96, 99–113 (1949).

Some compounds of the present invention Formula I exhibited $ED_{50}$'s in the Metrazol ® test of 5 to 30 mg/kg and $ED_{50}$'s in the electrical challenge test of about 10 to 30 mg/kg.

B. Muscle Relaxant Activity Test

The test procedure relied on to indicate positive muscle relaxant activity is the morphine-induced Straub Tail in Mice Test described by G. D. Novak in DRUG DEVELOPMENT RESEARCH 2, 383–386 (1982), except 8 animals per group were used per test rather than 10. The test is summarized as follows: The test drug, reference drug, and control articles to be administered are prepared in saline, 0.5% aqueous methylcellulose suspension or other, depending on solubility, in such concentration that the volume administered is 10 ml/kg. The initial screening dose of the test drug is usually 100 mg/kg. Groups of 8 mice are given an IP dose of the compound or vehicle prepared as described above. After 15 minutes, mice are administered morphine sulfate, 60 mg/kg, subcutaneously. Fifteen minutes after administration of morphine (i.e., 30 minutes after test compound administration), mice are scored for presence of Straub Tail (defined as an elevation of the tail at least 90 degrees from the horizontal). An $ED_{50}$ value may be determined from at least three logarithmically spaced doses by the method of Litchfield and Wilcoxon, J. PHARMACOL. EXP. THER. 96, 99–113 (1949). Compared to a reference compound, methocarbamol, which exhibited an $ED_{50}$ of 183.3 mg/kg, IP, in the above Straub Tail Test, some compounds of the present invention Formula I were 5–10 times more potent.

C. Antianxiety Activity Test

The test screening procedure relied on to indicate positive antianxiety response is a modification of the Vogel Conflict Test which is based on shock-suppressed drinking behavior in rats outlined in J. R. Vogel et al in PSYCHOPHARMACOLOGY, 21, 1–7 (1971). The procedure used is as follows: The test drug, reference drug and control articles are administered intraperitoneally in physiological saline, 0.5% aqueous methylcellulose or other medium depending on solubility, in such concentration that the volume administered is 5 ml/kg. The initial screening dose of the test drug is usually 100.0 mg/kg initially, and the reference drug, chlordiazepoxide at 7.5 mg/kg or diazepam at 5.62 mg/kg.

Prior to dosing, rats are housed 2 per cage and deprived of water for 48 hours and thereafter randomized into treatment groups of five. Feed is available ad libitum. Thirty minutes after dosing, each rat is placed individually in a plexiglass cage measuring 18 cm in width, 13 cm in height and 29.5 cm in length and equipped with a stainless steel grid floor. The cage is covered with a plastic lid containing holes to facilitate introduction of a water bottle (30 ml plastic centrifuge tube) with a rubber stopper and metal drinking tube. A Drinkometer circuit (Omnitech Electronics, Inc., 3000 Cortona Road, Columbus, Ohio 43204), is connected between the drinking tube and the grid floor of the apparatus so that the rat completes the circuit whenever it licks the tube. The procedure is to allow the rat to find the drinking tube and complete 20 licks (as displayed on the Drinkometer digital readout) prior to the start of the experimental session. Rats not reaching this criterion are discarded. A three minute experimental session is initiated by a 0.625 mA shock at the 20th lick. Rats that continue drinking will experience a shock at each successive 20th lick. The total number of shocks during the experimental session are recorded as follows:

$$\frac{\text{total licks}}{20} + 1 = \text{total shocks.}$$

Statistical analysis is performed by the Dunn's Multiple Comparison Test described by O. J. Dunn in TECHNOMETRICS 6(3), 241-252 (1964). The mean number of shocks experienced by the control group is compared with those of each drug-treated group. Significance is considered at $P<0.1$. The higher the total shocks compared to control, the more active is the compound. Active compounds may then be similarly tested at reduced dosages.

There is justification for the use of anticonvulsant testing as a screen for anxiolytic activity. Many of the clinically useful anxiolytic agents possess varying degrees of anticonvulsant activity (Randall and Schalleck, 1967). This effect has been observed in mice (Childress and Gluckman, 1964), rats (Baron et al, 1967), rabbits (Banziger, 1965), cats (Swinyard and Castillion, 1966), and humans (Rossi et al, 1973). Based on this evidence Lippa et al (1979) reported:

"The ability of a compound to prevent pentylenetetrazolinduced convulsions in mice is the most widely used initial screen test for anxiolytic action and has been shown to demonstrate a high degree of sensitivity and selectivity."

REFERENCES

Baron, F. A.; Vanderwert, C. A; Tedeschi, D. H. The synthesis and tranquilizer activity of 2- and 4-substituted 3,5-morpholinediones. J. Med. Chem., 10, 276-281 (1967).

Childress, S. J.; Gluckman, M. I. 1,4-Benzodiazepines. J. Pharm. Sci. 53, 577-590 (1964).

Lippa, A. S.; Nash, P. A.; Greenblatt, E. N. Pre-clinical neuropsychopharmacological testing procedures for anxiolytic drugs, in *Anxiolytics* (Ed: S. Fielding) Futura Publishing Co., Mt. Kisco, NY, pp 41-81, 1979.

Randall, L. O.; Schalleck, W. Pharmacological activity of certain benzodiazepines. In *Psychopharmacology: A Review of Progress* (Ed: D. H. Effron). U.S. Public Health Service Publication No. 1836, pp 153-184, 1967.

Rossi, G. F.; DiRocco, C.; Maira, G.; Meglio, M. Experimental and clinical studies of the anticonvulsant properties of a benzodiazepine derivative, clonazepam. In *The Benzodiazepines* (Eds: S. Garattini, E. Mussini, L. O. Randall), Raven Press, New York, pp 461-488, 1973.

Swinyard, E. A.; Castillion, A. W. Anticonvulsant properties of some benzodiazepines. J. Pharmacol. Exp. Ther. 151, 369-375 (1966).

TABLE

| Example No. Test Compound | Anticonvulsant Electroshock[1] | Test Data Metrazol[1] | Muscle-Relaxant Test Data[2] | Anxiolytic Test Data[3] |
|---|---|---|---|---|
| I | 100 (0) | 100 (0) | 100 (25) | NA (31.6) |
| III | 100 (12.5) | 100 (0) | 100 (25) | — |
| IV | 100 (0) | 100 (0) | 100 (0) | 31.6 |
| V | 100 (0) | 100 (0) | 100 (125) | 31.6 |
| VI | 100 (12.5) | 15.5 | 31.6 | 31.6 |
| VII | 100 (0) | 100 (25) | 100 (25) | NA (56.2) |
| VIII | 100 (0) | 100 (12.5) | 100 (37.5) | NA (56.2) |
| X | 100 (0) | 6.4 | 100 (62.5) | NA (56.2) |
| XI | 54.0 | 4.6 | 1.86 | — |
| XII | 100 (0) | 100 (25) | 100 (25) | NA (56.2) |
| XIII | 50.5 | 34.0 | 4.3 | NA (56.2) |
| XIV | 50.5 | 35.0 | 36.0 | NA (56.2) |
| XV | — | — | 100 (0) | — |
| XVI | — | — | 100 (0) | — |
| XVII | 100 (62.5) | 7.51 | 7.4 | NA (10) |
| XVIII | 24.05 | 3.16 | 2.1 | 31.6 |
| XIX | 100 (12.5) | 6.0 | 100 (25) | NA (31.6) |
| XX | 100 (0) | 43.6 | 100 (12.5) | NA (31.6) |
| XXI | 75.9 | 23.9 | 10.0 | NA (31.6) |

[1]Dose mg/kg IP (% protected)
[2]Dose mg/kg IP (% blocked)
[3]Dose (M.E.D.) mg/kg IP
NA = not active at dose tested (mg/kg)

What is claimed is:

1. A 2-phenylpyrazolo[1,5-a]pyrimidine-3-acetic acid or derivatives thereof corresponding to the formula:

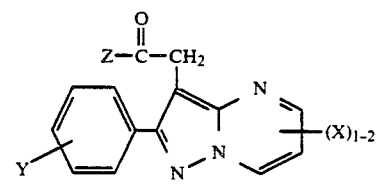

where X is hydrogen or a halogen, hydroxy, $C_1-C_4$ alkyl or $C_1-C_4$ alkoxy substituent; Y is hydrogen or a halogen, $C_1-C_4$ alkyl or $C_1-C_4$ alkoxy substituent; Z is a hydroxy, $C_1-C_4$ alkoxy or —NRR substituent; and R is, independently hydrogen or a $C_1$–$C_4$ alkyl substituent; or a pharmaceutically acceptable salt thereof.

2. A compound of claim 1 which is 2-Phenylpyrazolo[1,5-a]pyrimidine-3-acetic acid ethyl ester or a pharmaceutically acceptable salt thereof.

3. A compound of claim 1 which is 2-Phenylpyrazolo[1,5-a]pyrimidine-3-acetic acid or a pharmaceutically acceptable salt thereof.

4. A compound of claim 1 which is N,N-Dimethyl-2-phenylpyrazolo[1,5-a]pyrimidine-3-acetamide or a pharmaceutically acceptable salt thereof.

5. A compound of claim 1 which is N-Methyl-2-phenylpyrazolo[1,5-a]pyrimidine-3-acetamide or a pharmaceutically acceptable salt thereof.

6. A compound of claim 1 which is 2-Phenylpyrazolo[1,5-a]pyrimidine-3-acetamide or a pharmaceutically acceptable salt thereof.

7. A compound of claim 1 which is 2-Phenyl-N,N-dipropylpyrazolo[1,5-a]pyrimidine-3-acetamide or a pharmaceutically acceptable salt thereof.

8. A compound of claim 1 which is 2-(4-Chlorophenyl)pyrazolo[1,5-a]pyrimidine-3-acetic acid or a pharmaceutically acceptable salt thereof.

9. A compound of claim 1 which is 5,7-Dimethyl-2-phenylpyrazolo[1,5-a]pyrimidine-3-acetic acid ethyl ester or a pharmaceutically acceptable salt thereof.

10. A compound of claim 1 which is 2-(4-Chlorophenyl)pyrazolo[1,5-a]pyrimidine-3-acetic acid ethyl ester or a pharmaceutically acceptable salt thereof.

11. A compound of claim 1 which is 2-(4-Chlorophenyl)-N-methylpyrazolo[1,5-a]-pyrimidine-3-acetamide or a pharmaceutically acceptable salt thereof.

12. A compound of claim 1 which is 2-(4-Chlorophenyl)-N,N-methylpyrazolo[1,5-a]-pyrimidine-3-acetamide or a pharmaceutically acceptable salt thereof.

13. A compound of claim 1 which is 2-(4-Chlorophenyl)-5,7-dimethylpyrazolo[1,5-a]-pyrimidine-3-acetic acid ethyl ester or a pharmaceutically acceptable salt thereof.

14. A compound of claim 1 which is N,N,5,7-Tetramethyl-2-phenylpyrazolo[1,5-a]-pyrimidine-3-acetamide or a pharmaceutically acceptable salt thereof.

15. A compound of claim 1 which is N,5,7-Trimethyl-2-phenylpyrazolo[1,5-a]-pyrimidine-3-acetamide or a pharmaceutically acceptable salt thereof.

16. A compound of claim 1 which is 6-Chloro-2-(4-chlorophenyl)pyrazolo[1,5-a]-pyrimidine-3-acetic acid ethyl ester or a pharmaceutically acceptable salt thereof.

17. A compound of claim 1 which is 2-(4-Chlorophenyl)pyrazolo[1,5-a]pyrimidine-3-acetamide or a pharmaceutically acceptable salt thereof.

18. A compound of claim 1 which is 2-(4-Chlorophenyl)-N,N-dipropylpyrazolo[1,5-a]-pyrimidine-3-acetamide or a pharmaceutically acceptable salt thereof.

19. A compound of claim 1 which is 2-(4-Methylphenyl)-N,N-dipropylpyrazolo[1,5-a]-pyrimidine-3-acetamide or a pharmaceutically acceptable salt thereof.

20. A compound of claim 1 which is N-Methyl-2-(4-methylphenyl)pyrazolo[1,5-a]-pyrimidine-3-acetamide or a pharmaceutically acceptable salt thereof.

21. A compound of claim 1 which is 2-(4-Methylphenyl)pyrazolo[1,5-a]-pyrimidine-3-acetamide or a pharmaceutically acceptable salt thereof.

22. A compound of claim 1 which is N,N-Dimethyl-2-(4-methylphenyl)pyrazolo[1,5-a]pyrimidine-3-acetamide or a pharmaceutically acceptable salt thereof.

23. A method for the treatment of warm blooded animals for anxiety symptoms which comprises internally administering to said animals a symptoms alleviating effective amount of a 2-phenylpyrazolo[1,5-a]pyrimidine-3-acetic acid or derivatives thereof corresponding to the formula:

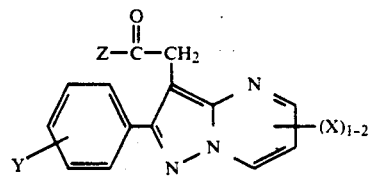

where X is hydrogen or a halogen, hydroxy, $C_1$–$C_4$ alkyl or $C_1$–$C_4$ alkoxy substituent; Y is hydrogen or a halogen, $C_1$–$C_4$ alkyl or $C_1$–$C_4$ alkoxy substituent; Z is a hydroxy, $C_1$–$C_4$ alkoxy or —NRR substituent; and R is, independently, hydrogen or a $C_1$–$C_4$ alkyl substituent; or a pharmaceutically acceptable salt thereof.

* * * * *